(12) United States Patent
Yousfi et al.

(10) Patent No.: US 7,090,860 B2
(45) Date of Patent: Aug. 15, 2006

(54) TOPICAL COMPOSITION

(75) Inventors: Naïma Yousfi, Paris (FR); Bertrand Piot, Paris (FR); Jérôme Senee, Lardy (FR)

(73) Assignee: L'Oreal, Paris (FR)

( * ) Notice: Subject to any disclaimer, the term of this patent is extended or adjusted under 35 U.S.C. 154(b) by 193 days.

(21) Appl. No.: 10/279,062

(22) Filed: Oct. 24, 2002

(65) Prior Publication Data
US 2003/0108579 A1 Jun. 12, 2003

(30) Foreign Application Priority Data
Oct. 25, 2001 (FR) .................................. 01 13818

(51) Int. Cl.
*A61K 8/02* (2006.01)
*A61K 8/18* (2006.01)
*A61K 8/00* (2006.01)

(52) U.S. Cl. .......................... 424/401; 424/59; 424/63; 424/64

(58) Field of Classification Search ................ 424/401, 424/59, 63, 64
See application file for complete search history.

(56) References Cited

U.S. PATENT DOCUMENTS

| 4,536,405 | A | * | 8/1985 | Nara et al. .................... 514/781 |
| 4,883,659 | A | * | 11/1989 | Goodman et al. ....... 424/78.03 |
| 5,843,407 | A | * | 12/1998 | El-Nokaly et al. ............ 424/64 |
| 6,017,548 | A | * | 1/2000 | Epstein et al. .............. 424/401 |
| 6,423,326 | B1 | * | 7/2002 | Shapiro ...................... 424/401 |
| 2003/0082129 | A1 | * | 5/2003 | Buckingham et al. ... 424/70.12 |

FOREIGN PATENT DOCUMENTS

| DE | 196 43 063 | 4/1998 |
| DE | 980 684 | 2/2000 |
| DE | 199 21 184 | 11/2000 |
| WO | WO 94/26234 | 11/1994 |
| WO | WO 99/59537 | 11/1999 |

\* cited by examiner

*Primary Examiner*—Sreeni Padmanabhan
*Assistant Examiner*—Marina Lamm
(74) *Attorney, Agent, or Firm*—Oblon, Spivak, McClelland, Maier & Neustadt, P.C.

(57) ABSTRACT

A composition containing a fatty phase containing at least one polyol ether, at least one oil and at least one wax, wherein the wax has a polarity which is the reverse of that of the oil.

44 Claims, No Drawings

TOPICAL COMPOSITION

FIELD OF THE INVENTION

The present invention relates to a composition comprising a fatty phase comprising (i) at least one polyol ether, (ii) at least one oil and (iii) at least one wax. Preferably, this composition is in stick form and is used as a make-up and/or care composition for keratinous materials such as the skin, the lips and/or superficial body growths.

BACKGROUND OF THE INVENTION

Compositions in solid form, particularly those in the form of a stick, generally contain waxes to solidify the composition and to aid in formation of a baton (stick). However, the presence of an excessively large amount of wax results in a stick composition which has inadequate cosmetic qualities such as, for example, difficulty in spreading and/or providing low deposition on the skin or the lips.

To improve the cosmetic properties of such stick compositions containing waxes, oils have been added in an attempt to obtain better spreading and deposition of the compositions. However, compositions containing wax and oil generally melt at temperatures of less than or equal to 37° C., which is problematic because such compositions are fragile. Also, such compositions have an oily appearance and exude strongly.

Efforts have been made to overcome these drawbacks by adding fillers which have the advantage of helping the stick compositions maintain their shape during a rise in temperature and improving the cosmetic qualities of the sticks. However, the addition of fillers may yield brittle and hard, or even sometimes rough, sticks.

OBJECTS OF THE INVENTION

The need therefore remains for a composition which may be provided in the form of a stick, which is temperature stable, particularly in ovens, and which does not exhibit exudation during a rise in temperature, but which can be deposited on the keratinous material to which it is applied, for example the skin or the lips, even in the absence of fillers.

SUMMARY OF THE INVENTION

It has now been discovered, surprisingly, that the addition of a polyol ether to a mixture of oil and wax yields a composition which does not melt at temperatures of less than or equal to 37° C., but which spreads well and deposits well on the lips or the skin. Additionally, the composition possesses good cosmetic properties, particularly not giving a sensation of dryness when it is applied to the skin. The composition according to the invention may be advantageously used, for example, to treat the symptoms linked to drying of the skin and/or of the lips.

DETAILED DESCRIPTION OF THE INVENTION

According to preferred embodiments of the present invention, a solid composition comprising, in a physiologically acceptable medium, at least one fatty phase comprising at least one polyol ether, at least one oil and at least one wax having a polarity which is the reverse of that of the oil is provided.

Using a wax having a "polarity which is the reverse of that of the oil" means here that when the composition comprises a polar oil, it should contain at least one apolar wax, and that, when the composition comprises an apolar oil, it should contain at least one polar wax. When the composition comprises both a polar oil and an apolar oil, it should comprise at least one apolar wax.

In accordance with the present invention, properties of stability and disintegration (spreading and deposition on the lips or the skin) are believed to be linked to a certain hardness of the composition, a hardness which is linked to the shearing force. Preferably, the hardness and the shearing force of the composition are such that the composition is self-supported: that is, the composition supports itself by remaining in its solid form (for example, stick form) and does not collapse under its own weight as do creams or liquids, and the composition can easily disintegrate to form a satisfactory deposit on the skin and/or the lips. The hardness of the compositions obtained is measured at 20° C. using a DFGHS 2 dynamometer from the company INDELCO-CHATILLON, moving at a speed of 100 mm/minute. It is expressed as the shearing force (expressed in grams) necessary to cut a stick 12.7 mm in diameter under these conditions. In accordance with the present invention, the shearing force for the composition preferably ranges from 100 to 300 g, more preferably from 120 to 250 g, and most preferably from 150 to 220 g.

Thus, according to a preferred embodiment of the present invention, a solid composition is provided comprising, in a physiologically acceptable medium, at least one fatty phase comprising at least one polyol ether, at least one wax and at least one oil, the composition having a shearing force ranging from 100 to 300 g.

In general, the composition according to the present invention constitutes a solid composition and it may be provided in the form of a cast product, a stick, or a product in a dish.

According to preferred embodiments, the solid composition according to the present invention is intended for topical application, preferably to the skin, the lips and/or superficial body growths. Accordingly, the composition comprises a physiologically acceptable medium. The expression "physiologically acceptable medium" is understood here to mean a medium which is nontoxic and capable of being applied to the skin (including the inside of the eyelids), the lips, the nails or the hair of human beings. The composition of the invention may constitute in particular a cosmetic or dermatological composition.

Moreover, the phrase "solid composition" is understood to mean any composition which does not flow under its own weight which preferably has a hardness as defined above (shearing force of 100 to 300 g).

The composition of the present invention preferably comprises a single fatty phase, and this fatty phase is preferably a continuous phase.

The compositions of the present invention may be anhydrous compositions, that is to say free of water and/or of hydrophilic compounds. However, they may also contain up to 10% by weight of a hydrophilic phase relative to the total weight of the composition, preferably 1 to 5% by weight of hydrophilic phase, and more preferably from 1 to 2% by weight of hydrophilic phase relative to the total weight of the composition. The hydrophilic phase may contain water alone, or water and hydrophilic and water-soluble additives such as polyols, gelling agents and/or active agents. If this hydrophilic phase is present, it is preferably dispersed in the fatty phase which forms a continuous phase.

According to particularly preferred embodiments of the present invention, the composition is anhydrous, that is to say that it contains only the fatty phase, or is practically anhydrous, that is to say that it contains less than 5% by weight of water and/or hydrophilic or water-soluble additives.

In the composition according to the present invention, the polyol ether may be chosen from, among other ethers, ethers of pentaerythritol and of polyalkylene glycol, ethers of a fatty alcohol and of sugar, and mixtures thereof.

The ethers of pentaerythritol and of polyalkylene glycol may contain from 1 to 450 oxyalkylenated units, preferably from 1 to 200 oxyalkylenated units, more preferably from 1 to 100 oxyalkylenated units and most preferably from 1 to 50 oxyalkylenated units. They may be chosen from, among other ethers, the ethers of pentaerythritol and of polyethylene glycol containing from 1 to 450 oxyethylenated units, preferably from 1 to 200 oxyethylenated units, more preferably from 1 to 100 oxyethylenated units and most preferably from 1 to 50 oxyethylenated units; the ethers of pentaerythritol and of polypropylene glycol containing from 1 to 450 oxypropylenated units, preferably from 1 to 200 oxypropylenated units, more preferably from 1 to 100 oxypropylenated units and most preferably from 1 to 50 oxypropylenated units; and mixtures thereof. According to a preferred embodiment of the present invention, the polyol ether is selected from the group consisting of the ether of pentaerythritol and of polyethylene glycol containing 5 oxyethylenated (OE) units (CTFA name: PEG-5 Pentaerythrityl Ether), the ether of pentaerythritol and of polypropylene glycol containing 5 oxypropylenated (5 OP) units (CTFA name: PPG-5 Pentaerythrityl ether), and mixtures thereof, particularly the PEG-5 Pentaerythrityl Ether, PPG-5 Pentaerythrityl ether and soya bean oil mixture marketed under the name "Lanolide" by the company Vevy, where the constituents are in a 46/46/8 weight ratio: 46% of PEG-5 Pentaerythrityl Ether, 46% of PPG-5 Pentaerythrityl Ether and 8% of soya bean oil.

The ethers of a fatty alcohol and of a sugar may be chosen from, among other ether, the group consisting of ethers or mixtures of ethers of a $C_8$–$C_{22}$ fatty alcohol and of glucose, maltose, sucrose or fructose; ethers or mixtures of ethers of a $C_{14}$–$C_{22}$ fatty alcohol and of methylglucose; and mixtures thereof.

The $C_8$–$C_{22}$ or $C_{14}$–$C_{22}$ fatty alcohols forming the fatty unit of the sugar ethers may contain a saturated or unsaturated linear alkyl chain containing from 8 to 22 or from 14 to 22 carbon atoms, respectively. The fatty unit of the ethers resulting from the fatty alcohol are preferably chosen from the decyl, cetyl, behenyl, arachidyl, stearyl, palmityl, myristyl, lauryl, capryl and hexadecanyl units, and mixtures thereof such as cetearyl (mixture of cetyl and stearyl).

Examples of ethers of a fatty alcohol and of a sugar include, for example, alkyl polyglucosides (APG) such as decyl glucoside and lauryl glucoside marketed, for example, by the company Henkel under the respective names Plantaren 2000 and Plantaren 1200; cetearyl glucoside, optionally combined with cetearyl alcohol, the mixture being marketed, for example, under the name Montanov 68 by the company Seppic (where the constituents are in a 12/46/42 ratio: 12% of cetearyl glucoside, 46% of cetyl alcohol and 42% of stearyl alcohol); stearyl glucoside, which is marketed under the name Tegocare CG90 by the company Goldschmidt and under the name Emulgade KE3302 by the company Henkel; and arachidyl glucoside, for example in the form of the mixture of arachidyl and behenyl alcohols and of arachidyl glucoside, marketed under the name Montanov 202 by the company Seppic. Other examples include branched or unsaturated chain alkyl polyglucosides such as isostearyl glucoside, optionally as a mixture with isostearyl alcohol, marketed for example under the name Montanov WO18 by the company Seppic; and oleyl glucoside, optionally as a mixture with oleyl alcohol, marketed by the company Seppic. It is also possible to use a mixture of alkyl polyglucosides as defined above. According to a preferred embodiment of the present invention, the mixture of alkyl polyglucoside as defined above with the corresponding fatty alcohol may be in the form of a self-emulsifying composition such as, for example, those described in PCT publication no. WO-A-92/06778.

The quantity of polyol ether(s) present may vary widely, and it may range, for example, from 0.5 to 40%, preferably from 1 to 30%, and more preferably from 5 to 25% by weight relative to the total weight of the composition.

The fatty phase of the composition according to the present invention comprises at least one oil. The term "oil" is understood to mean any physiologically acceptable non-aqueous liquid medium at room temperature (25° C.) and atmospheric pressure (760 mmHg). The quantity of oil(s) present may range, for example, from 20 to 80%, preferably from 30 to 70%, by weight relative to the total weight of the composition.

Acceptable oils include hydrocarbon and/or silicone and/or fluorinated oils.

They may be of animal, plant, inorganic or synthetic origin. The phrase "hydrocarbon oil" is understood to mean any oil containing predominantly carbon and hydrogen atoms, and optionally ester, ether, fluorinated, carboxylic acid and/or alcohol groups. In addition, acceptable oils may be volatile and/or nonvolatile. The phrase "volatile oil" is understood to mean an oil capable of evaporating at room temperature from a support to which it has been applied; in other words, an oil having a measurable vapour pressure at 25° C. and 1 atmosphere, for example, greater than 0 Pa, preferably ranging from $10^{-3}$ to 300 mmHg (0.13 Pa to 40 000 Pa). Examples of acceptable volatile oils include volatile silicone oils such as cyclic or linear volatile silicones. Examples of other acceptable volatile oils include volatile hydrocarbon oils such as isoparaffins and volatile fluorinated oils. Among the oils which may be used in accordance with the present invention, some are polar and others are apolar (that is, nonpolar).

The polar oils contain in their chemical structure at least one nonionic or ionic polar group, and preferably at least two nonionic or ionic polar groups such as, for example, the following groups:

—COOH;

—mono- or disubstituted (primary or secondary) OH;

—$PO_4$;

—NHR; $NR_1R_2$, $R_1$ and $R_2$ optionally forming a ring and representing a linear or branched $C_1$ to $C_{20}$ alkyl or alkoxy radical, or

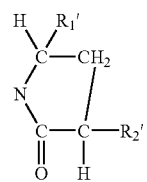

where $R_1'$ and $R_2'$ may represent hydrogen or a linear or branched $C_1$ to $C_{20}$ alkyl or alkoxy chain.

The polarity may be described by the Hansen solubility parameter δa. Indeed, this parameter characterizes, for a given constituent, the energy corresponding to the polar interactions (δp) and the interactions of the hydrogen bond type (δh) existing between the molecules of these constituents.

$$\delta_a = \sqrt{\delta_p^2 + \delta_h^2}$$

The apolar oils have a δa value equal to 0. Suitable apolar oils include:

silicone oils, such as linear or cyclic, volatile or nonvolatile polydimethylsiloxanes (PDMS) which are liquid at room temperature; phenylated silicones such as phenyltrimethicones, phenyldimethicones, phenyltrimethylsiloxydiphenylsiloxanes, diphenyldimethicones, diphenylmethyldiphenyltrisiloxanes, 2-phenylethyl trimethylsiloxysilicates;

linear or branched hydrocarbons of synthetic or inorganic origin such as volatile or nonvolatile paraffin oils, and derivatives thereof; liquid petroleum jelly; liquid lanolin; polydecenes; hydrogenated polyisobutene such as Parleam® oil; squalane; hydrogenated isoparaffin; isohexadecane; isododecane;

and mixtures thereof.

The polar oils have a δa value different from 0, that is, greater than 0. Acceptable polar oils include:

oils of plant origin, hydrocarbon oils with a high content of triglycerides consisting of esters of fatty acids and of glycerol in which the fatty acids may have varied chain lengths from $C_4$ to $C_{24}$, it being possible for the latter to be linear or branched, saturated or unsaturated. Examples of acceptable oils of plant origin include jojoba, wheat germ, maize, sunflower, karite butter, castor, sweet almond, macadamia, apricot, soya bean, cottonseed, lucerne, poppyseed, pumpkinseed, sesame, gourd, rapeseed, avocado, hazelnut, grapeseed or blackcurrant seed, evening primrose, millet, barley, quinoa, olive, rye, safflower, candlenut, passionflower, rose-muscat and coriander oils; alternatively, triglycerides of caprylic/capric acids such as those sold by the company Stearineries Dubois or those sold under the names Miglyol 810, 812 and 818 by the company Dynamit Nobel;

synthetic oils or synthetic esters of formula $R_5COOR_6$ in which $R_5$ represents the residue of a linear or branched fatty acid containing from 1 to 40 carbon atoms and $R_6$ represents a hydrocarbon chain, preferably a branched hydrocarbon chain, containing from 1 to 40 carbon atoms provided that $R_5+R_6$ is $\geq 10$, such as for example, Purcellin oil (ketostearyl octanoate), isononyl isononanoate, $C_{12}$ to $C_{15}$ alcohol benzoate, isopropyl myristate, 2-ethylhexyl palmitate, isostearyl isostearate, isopropyl isostearate, octanoates, decanoates or ricinoleates of alcohols or of polyalcohols; hydroxylated esters such as isostearyl lactate, diisostearyl maleate; $C_{12}$–$C_{15}$ alkyl benzoate; and esters of pentaerythritol;

synthetic ethers having from 10 to 40 carbon atoms;

$C_8$ to $C_{26}$ fatty alcohols such as oleyl alcohol, isostearyl alcohol and octyldodecanol;

mixtures thereof.

The fatty phase of the composition according to the present invention comprises at least one wax. A wax, for the purposes of the present invention, is preferably a lipophilic fatty compound, solid at room temperature (25° C.), with a reversible solid/liquid change of state, having a melting point which is greater than 40° C. and which may be as high as 200° C., and which has, in the solid state, anisotropic crystalline organization.

Any type of wax may be used in accordance with the present invention. Acceptable waxes include, for example, waxes of natural origin, in particular of plant or animal origin, waxes of inorganic origin, waxes of synthetic origin, and mixtures thereof. Examples of acceptable waxes include beeswax, Montan wax, Carnauba wax, Candelilla wax, Chinese wax, flax wax, pine wax, cotton wax, Ouricoury wax, lignite wax, rice bran wax, sugar cane wax, Japan wax, cork fibre wax, paraffin waxes, microcrystalline waxes, lanolin wax, ozokerites, hydrogenated oils having a melting point greater than 40° C. (approximately), such as hydrogenated jojoba oil, polyethylene waxes which are derived from the polymerization of ethylene, waxes obtained by Fischer-Tropsch synthesis, esters of fatty acids and glycerides which are concrete (i.e. solid) at 40° C., silicone waxes such as alkyl, alkoxy and/or esters of poly(di)methylsiloxane which are solid at 40° C.; and mixtures thereof.

As indicated above, when the composition comprises a polar oil, it should contain at least one apolar wax. When the composition comprises an apolar oil, it should contain at least one polar wax. When the composition comprises a polar oil and an apolar oil, it should comprise at least one apolar wax.

As indicated above for the oils, the polarity may be described by the Hansen solubility parameter δa according to the equation indicated above.

The so-called apolar waxes have a δa value equal to 0. Preferably, apolar waxes are hydrocarbon waxes or silicone waxes. Examples of acceptable hydrocarbon waxes include, for example, microcrystalline waxes, ozokerite, paraffin waxes, and polyethylene waxes (which are nonmodified).

The so-called polar waxes are waxes containing polar groups as indicated above for the oils, and they have a δa value greater than 0. Preferably, polar waxes are waxes of animal origin, waxes of plant origin, waxes of synthetic origin containing polar groups and silicone waxes containing polar groups. Examples of acceptable polar waxes include, for example, Montan wax, Carnauba wax, Candelilla wax, Chinese wax, flax wax, pine wax, cotton wax, Ouricoury wax, lignite wax, rice bran wax, sugar cane wax, Japan wax, cork fibre wax, polyglycerolated beeswaxes, hydrogenated oils, esters of fatty acids and glycerides which are concrete at 40° C. (i.e. solid at 40° C.), and silicone waxes containing one or more ester groups.

The total quantity of (polar and/or apolar) wax(es) present may range, for example, from 5 to 40%, preferably from 10 to 30%, by weight relative to the total weight of the composition.

According to a preferred embodiment of the present invention, the composition comprises at least one microcrystalline wax and at least one polar oil, preferably one oil chosen from oils of plant origin, fatty alcohols, and mixtures thereof, and more preferably chosen from octyldodecanol, karite butter oil, castor oil, avocado oil and mixtures thereof. Such a composition may also comprise one or more apolar oils such as, for example, linear or branched hydrocarbons, such as polydecenes and Parleam oil, and/or one or more other polar or apolar waxes.

As indicated above, the composition of the present invention may comprise from 0 to 10% by weight of a hydrophilic phase, relative to the total weight of the composition, preferably from 1 to 5% by weight, which may comprise water and/or hydrophilic or water-soluble additives (active agents and/or gelling agents for example). Preferably, the hydrophilic phase may comprise moisturizers such as glycerin. The hydrophilic constituents which may be present are preferably dispersed in the fatty phase containing oils and waxes.

The composition according to the present invention may also comprise a particulate phase. The quantity of particulate phase may range, for example, from 0 to 30%, preferably from 0 to 20%, by weight relative to the total weight of the composition. When a particulate phase is present, its quantity is generally at least 0.05% by weight relative to the total weight of the composition. The quantity of particulate phase may range, for example, from 0.05 to 30%, preferably from 1 to 20%, by weight relative to the total weight of the composition. This particulate phase may comprise particles chosen from pigments, pearlescent agents, fillers, and mixtures thereof. These pigments, pearlescent agents and fillers are chosen from those usually used in cosmetic compositions. The term "pigments" should be understood to mean white or coloured, inorganic or organic particles intended to colour and/or opacify the composition. The term "fillers" should be understood to mean colourless or white, inorganic or synthetic, lamellar or nonlamellar particles intended to give body or stiffness to the composition, and/or smoothness, mattness and/or uniformity to the make-up. The term "pearlescent agents" should be understood to mean iridescent particles which reflect light.

The pigments may be white or coloured, inorganic and/or organic, of micrometric or nanometric size. Suitable inorganic pigments include, for example, titanium, zirconium or cerium dioxides, and zinc, iron or chromium oxides, ferric blue. Suitable organic pigments include, for example, carbon black, and barium, strontium, calcium and aluminium lacquers.

Suitable pearlescent agents include, for example, mica coated with titanium oxide, iron oxide, a natural pigment or bismuth oxychloride, and coloured mica-titanium.

The fillers may be inorganic or synthetic, lamellar or nonlamellar. Suitable fillers include, for example, talc, mica, silica, kaolin, nylon powders, polyethylene powders, Teflon, modified or nonmodified starch, mica-titanium, natural pearlescent agent, boron nitride, microspheres such as Expancel (Nobel Industrie), Polytrap (Dow Corning) and microbeads of silicone resin (Tospearls from Toshiba, for example).

Advantageously, the composition according to the present invention comprises at least one colouring substance such as, for example, lipophilic colorants or the hydrophilic colorants usually used in cosmetic or dermatological compositions; the pigments and pearlescent agents described above; and mixtures thereof. This colouring substance is generally present in an amount of 0.01 to 40%, preferably from 5 to 25%, by weight relative to the total weight of the composition.

The composition according to the invention may comprise, in addition, any additive customarily used in the field considered, in particular the cosmetic field, such as antioxidants; perfumes; essential oils; preservatives; cosmetic active agents; vitamins such as vitamin E (tocopherol) and its derivatives (for example acetate), vitamin A (retinol) and its derivatives (for example retinyl palmitate), vitamin C (ascorbic acid) and its derivatives (for example ascorbyl palmitate), the derivatives of these vitamins being in particular esters including the palmitate and the acetate; essential fatty acids; sphingolipids and ceramides; self-tanning compounds such as DHA (dihydroxyacetone); sunscreens such as, for example, octyl methoxycinnamate (Parsol MCX), 3-benzophenone (Uvinul M40), butylmethoxydibenzoylmethane (Parsol 1789); surfactants; polymers; and mixtures thereof. These additives may be present in the composition in an amount of 0 to 20% by weight relative to the total weight of the composition. Of course, persons skilled in the art would be careful to choose this or these possible additional compounds, and/or their quantity, such that the advantageous properties of the composition according to the invention are not, or not substantially, impaired by the envisaged addition.

As indicated above, the composition according to the invention is preferably provided in solid form. This means that no collapse of the composition outside the container comprising it is observed in the absence of a mechanical or thermal stimulation (heating in particular).

The methods for making the compositions according to the invention are not in any way different from the methods conventionally used in cosmetics which are known to persons skilled in the art.

The compositions according to the present invention may constitute a care product and/or a make-up product for keratinous material, preferably the skin, the lips and/or superficial body growths such as the nails, the eyelashes, the eyebrows and the hair. The make-up products are most often coloured and generally contain pigments. Examples of acceptable make-up products include, for example, a foundation, a lipstick, a blusher, an eyeshadow, a mascara or an eyeliner.

The compositions of the present invention may be in the form of a cast powder, a product in a dish (foundation, blusher, eyeshadow), or a product in the form of a baton (lipstick or stick for the care of the lips). According to a preferred embodiment, the compositions are in the form of a baton (stick), preferably for the care of the lips or as make-up for the lips as lipstick.

The composition of the present invention may also be used for the care and/or the treatment of the skin, the lips and/or superficial body growths, for example, for moisturizing the lips and/or for the treatment of chapped and/or dry lips.

Accordingly, the present invention is also directed to the cosmetic use of a cosmetic composition as defined above, for the care and/or the treatment of the skin, the lips and/or superficial body growths, preferably for moisturizing the lips.

The subject of the present invention also includes the cosmetic use of a cosmetic composition as defined above, as make-up f6r the skin, the lips and/or superficial body growths.

The subject of the present invention also includes a cosmetic method for treating chapped and/or dry lips, comprising applying to the lips a cosmetic composition as defined above.

The invention is illustrated in greater detail in the following examples, in which the percentages are given by weight, unless otherwise stated.

EXAMPLE 1

Care Stick

| | |
|---|---|
| Lanolide | 15% |
| Microcrystalline wax | 15% |
| Ozokerite | 5% |
| Polar oil (castor oil) | 35% |

-continued

| | |
|---|---|
| Nonpolar oil (Parleam oil) | 27% |
| Screening agent (Parsol MCX) | 1% |
| Vitamin E | 1% |
| Perfume | 1% |

Procedure: The lanolide, the oils and the active agents (screening agent, vitamin E and perfume) (phase A) are heated to around 85° C., with stirring. The waxes (phase B) are heated to around 100° C. After complete melting of the waxes, phase A is added to phase B. The mixture obtained is then poured into moulds and cooled to room temperature.

A stable cast product is obtained (good temperature stability), having good cosmetic properties (good deposition on the skin or the lips and smoothness) and which can be used, for example, for protecting the lips and for avoiding their becoming dry.

EXAMPLE 2

Care Stick

| | |
|---|---|
| Lanolide | 13% |
| Microcrystalline wax | 20% |
| Ozokerite | 5% |
| Polar oil (castor oil) | 32% |
| Nonpolar oil (polydecene) | 27% |
| Ascorbyl palmitate | 1% |
| Vitamin E | 1% |
| Perfume | 1% |

The procedure is identical to that for Example 1.

A stable stick is obtained (good temperature stability), having good cosmetic properties (good deposition on the skin or the lips and smoothness) and which can be used, for example, for treating chapped lips.

EXAMPLE 3

Care Stick

| | |
|---|---|
| Montanov 68 | 17% |
| Microcrystalline wax | 15% |
| Polyglycerolated beeswax | 5% |
| Polar oil (castor oil) | 15% |
| Polar oil (avocado oil) | 20% |
| Nonpolar oil (Parleam oil) | 25% |
| Ascorbyl palmitate | 1% |
| Retinyl palmitate | 1% |
| Perfume | 1% |

The procedure is identical to that for Example 1.

A stable stick is obtained (good temperature stability), having good cosmetic properties (good deposition on the skin or the lips and smoothness) and which can be used, for example, for treating dry lips.

EXAMPLE 4

Lipstick

| | |
|---|---|
| Lanolide | 20% |
| Microcrystalline wax | 17% |
| Polar oil (octyldodecanol) | 21% |
| Nonpolar oil (Parleam oil) | 20% |
| Nonpolar oil (polydecene) | 10% |
| CI 77491 (brown colorant) | 11% |
| Allantoin | 0.5% |
| Tocopherol acetate | 0.5% |

The procedure is identical to that for Example 1.

A stable coloured stick is obtained (good temperature stability), having good cosmetic properties (good deposition on the skin or the lips and smoothness) and which can be used as lipstick.

The present application claims priority from French patent application no. 0113818, filed Oct. 25, 2001, the entire disclosure of which is hereby incorporated by reference. Also, all publications, patents and other documents disclosed herein are hereby incorporated by reference as well.

The invention claimed is:

1. A solid composition comprising, in a physiologically acceptable medium, at least one fatty phase comprising (i) at least one polyol ether selected from the group consisting of the ether of pentaerythritol and of polyethylene glycol containing 5 oxyethylenated units, the ether of pentaerythritol and of polypropylene glycol containing 5 oxypropylenated units, and mixtures thereof, (ii) at least one oil and (iii) at least one wax, wherein said wax has a polarity which is the reverse of that of the oil and wherein the quantity of polyol ether ranges from 0.5 to 40% by weight relative to the total weight of the composition.

2. The composition according to claim 1, wherein the composition has a shearing force ranging from 100 to 300 g.

3. The composition according to claim 1, wherein the composition has a shearing force ranging from 120 to 250 g.

4. The composition according to claim 1, wherein the composition has a shearing force ranging from 150 to 220 g.

5. The composition according to claim 1, wherein the polyol ether is a mixture of an ether of pentaerythritol and of polyethylene glycol containing 5 oxyethylenated units and of an ether of pentaerythritol and of polypropylene glycol containing 5 oxypropylenated units.

6. The composition according to claim 5, wherein the at least one oil is soya bean oil.

7. The composition according to claim 1, wherein the quantity of polyol ether ranges from 1 to 30% by weight relative to the total weight of the composition.

8. The composition according to claim 1, wherein the quantity of oil ranges from 20 to 80% by weight relative to the total weight of the composition.

9. The composition according to claim 1, wherein the quantity of oil ranges from 30 to 70% by weight relative to the total weight of the composition.

10. The composition according to claim 1, wherein the at least one oil is an apolar oil chosen from the group consisting of silicone oils, linear or branched hydrocarbons, and mixtures thereof.

11. The composition according to claim 1, wherein the at least one oil is a polar oil chosen from the group consisting of oils of plant origin; synthetic oils or synthetic esters of the formula $R_5COOR_6$ in which $R_5$ represents the residue of a linear or branched fatty acid containing from 1 to 40 carbon atoms, and $R_6$ represents a hydrocarbon chain containing from 1 to 40 carbon atoms provided that $R_5+R_6$ is $\geqq 10$; synthetic ethers; $C_8$ to $C_{26}$ fatty alcohols; and mixtures thereof.

12. The composition according to claim 11, wherein the at least one polar oil is selected from the group consisting of castor oil, avocado oil, octyldodecanol, and mixtures thereof.

13. The composition according to claim 10, wherein the at least one apolar oil is selected from the group consisting of hydrogenated polyisobutene, polydecene, and mixtures thereof.

14. The composition according to claim 1, wherein the at least one wax is selected from the group consisting of waxes of natural origin, waxes of inorganic origin, waxes of synthetic origin, and mixtures thereof.

15. The composition according to claim 14, wherein the at least one wax is selected from the group consisting of beeswax, Montan wax, Carnauba wax, Candelilla wax, Chinese wax, flax wax, pine wax, cotton wax, Ouricoury wax, lignite wax, rice bran wax, sugar cane wax, Japan wax, cork fibre wax, paraffin waxes, microcrystalline waxes, lanolin wax, ozokerites, hydrogenated oils having a melting point greater than 40° C., polyethylene waxes, waxes obtained by Fischer-Tropsch synthesis, esters of fatty acids and glycerides which are solid at 40° C., silicone waxes and mixtures thereof.

16. The composition according to claim 15, wherein the at least one wax is selected from the group consisting of microcrystalline waxes, ozokerites, beeswaxes, polyethylene waxes, candelilla waxes and mixtures thereof.

17. The composition according to claim 16, wherein the at least one wax is selected from the group consisting of microcrystalline waxes, ozokerites, and mixtures thereof.

18. The composition according to claim 1, wherein the quantity of wax ranges from 5 to 40% by weight relative to the total weight of the composition.

19. The composition according to claim 1, wherein the quantity of wax ranges from 10 to 30% by weight relative to the total weight of the composition.

20. The composition according to claim 1, comprising at least one microcrystalline wax and at least one polar oil selected from the group consisting of oils of plant origin, fatty alcohols, and mixtures thereof.

21. The composition according to claim 1, wherein the composition is anhydrous.

22. The composition according to claim 1, wherein the composition comprises a hydrophilic phase.

23. The composition according to claim 22, wherein the hydrophilic phase comprises ingredients selected from the group consisting of water, hydrophilic additives, water-soluble additives, and mixtures thereof.

24. The composition according to claim 1, wherein the composition comprises a particulate phase.

25. The composition according to claim 24, wherein the particulate phase comprises particles selected from the group consisting of pigments, pearlescent agents, fillers, and mixtures thereof.

26. The composition according to claim 1, wherein the composition comprises at least one colouring substance.

27. The composition according to claim 1, wherein the composition is in the form of a stick.

28. The composition according to claim 1, wherein the composition comprises a sunscreen agent.

29. The composition according to claim 1, wherein the composition comprises an active agent.

30. The composition according to claim 1, wherein the composition is in the form of a make-up product.

31. The composition according to claim 1, wherein the composition is in the form of a lipstick.

32. The composition according to claim 1, wherein the composition is in the form of a lip care product.

33. The composition according to claim 1, wherein the composition is in the form of a foundation.

34. The composition according to claim 1, wherein the at least one wax is a polar wax and the at least one oil is an apolar oil.

35. The composition according to claim 1, wherein the at least one wax is an apolar wax and the at least one oil is a polar oil.

36. A method of caring for and/or treating the skin, the lips and/or superficial body growths comprising applying the composition according to claim 1 to the skin, the lips and/or superficial body growths.

37. A method of moisturizing the lips comprising applying the composition according to claim 1 to the lips.

38. A method of making-up the skin, the lips and/or superficial body growths comprising applying the composition according to claim 1 to the skin, the lips and/or superficial body growths.

39. A method of treating chapped and/or dry lips comprising applying to the lips a composition according to claim 1.

40. The composition according to claim 1, wherein the quantity of polyol ether ranges from 5 to 25% by weight relative to the total weight of the composition.

41. The composition according to claim 1, wherein the quantity of polyol ether ranges from 12 to 18% by weight relative to the total weight of the composition.

42. The composition according to claim 5, wherein the quantity of polyol ether ranges from 1 to 30% by weight relative to the total weight of the composition.

43. The composition according to claim 5, wherein the quantity of polyol ether ranges from 5 to 25% by weight relative to the total weight of the composition.

44. The composition according to claim 5, wherein the quantity of polyol ether ranges from 12 to 18% by weight relative to the total weight of the composition.

* * * * *